(12) United States Patent
Hansen et al.

(10) Patent No.: US 12,392,768 B2
(45) Date of Patent: Aug. 19, 2025

(54) METHODS FOR DETERMINING BLOOD GAS OR METABOLIC PARAMETERS

(71) Applicant: RADIOMETER MEDICAL APS, Brønshøj (DK)

(72) Inventors: Thomas Steen Hansen, Brønshøj (DK); Ida Hollesen, Brønshøj (DK); Melanie Andrea Burkhardt, Brønshøj (DK)

(73) Assignee: RADIOMETER MEDICAL APS (DK)

( * ) Notice: Subject to any disclaimer, the term of this patent is extended or adjusted under 35 U.S.C. 154(b) by 0 days.

(21) Appl. No.: 17/606,511

(22) PCT Filed: May 14, 2020

(86) PCT No.: PCT/EP2020/063409
§ 371 (c)(1),
(2) Date: Oct. 26, 2021

(87) PCT Pub. No.: WO2020/229580
PCT Pub. Date: Nov. 19, 2020

(65) Prior Publication Data
US 2022/0205975 A1    Jun. 30, 2022

(30) Foreign Application Priority Data

May 14, 2019    (DK) .......................... PA 2019 00579

(51) Int. Cl.
*G01N 33/49* (2006.01)
*G01N 1/38* (2006.01)
(Continued)

(52) U.S. Cl.
CPC ........... *G01N 33/4925* (2013.01); *G01N 1/38* (2013.01); *G01N 1/42* (2013.01); *G01N 15/14* (2013.01);
(Continued)

(58) Field of Classification Search
CPC ........ G01N 33/4925; G01N 1/38; G01N 1/42; G01N 15/14; G01N 2015/14; G01N 2015/1486
See application file for complete search history.

(56) References Cited

U.S. PATENT DOCUMENTS 3,963,440 A * 6/1976 Stein ................ G01N 35/00594
204/402
5,342,498 A    8/1994 Graves et al.
(Continued)

FOREIGN PATENT DOCUMENTS

EP    0 520 443 B1    1/1997
EP    1986007 A1 * 10/2008 ......... G01N 33/4915
(Continued)

OTHER PUBLICATIONS

Trulock, E. Arterial Blood Gas, 1990, Butterworths, 3rd edition, pp. 254-257 (Year: 1990).*
(Continued)

*Primary Examiner* — Jill A Warden
*Assistant Examiner* — Alex Ramirez
(74) *Attorney, Agent, or Firm* — FROST BROWN TODD LLP

(57) ABSTRACT

The present invention relates to methods for determining a blood gas parameter and/or a basic metabolic panel parameter in a blood sample comprising combining the blood sample with an anti-coagulant and an anti-platelet agent, and determining said blood gas parameter and/or parameter in the sample. In some aspects, the invention relates to determining said parameters in samples that have been subjected to pre-analytical stress.

20 Claims, 6 Drawing Sheets

(51) Int. Cl.
    *G01N 1/42* (2006.01)
    *G01N 15/01* (2024.01)
    *G01N 15/14* (2024.01)
(52) U.S. Cl.
    CPC .............. *G01N 2015/016* (2024.01); *G01N 2015/1486* (2013.01)

(56) References Cited

U.S. PATENT DOCUMENTS

| | | | |
|---|---|---|---|
| 6,880,384 B2 | 4/2005 | Hvidtfeldt et al. | |
| 2003/0126914 A1* | 7/2003 | Hvidtfeldt | B01F 31/23 73/53.01 |
| 2009/0263781 A1* | 10/2009 | Sehgal | A01N 1/02 435/2 |
| 2011/0002526 A1 | 1/2011 | Atomique | |
| 2013/0209985 A1* | 8/2013 | Hoke | A61B 5/150755 435/307.1 |
| 2017/0000414 A1* | 1/2017 | Cho | A61B 5/02035 |

FOREIGN PATENT DOCUMENTS

| | | | |
|---|---|---|---|
| JP | 3002903 B2 | 1/2000 | |
| JP | 2000-074911 A | 3/2000 | |
| JP | 2000-146956 A | 5/2000 | |
| JP | 2015-206609 A | 11/2015 | |
| JP | 2019-207229 A | 12/2019 | |
| JP | 2019-211216 A | 12/2019 | |
| JP | 2021-501336 A | 1/2021 | |
| JP | 2021-192046 A | 12/2021 | |
| WO | WO 2011/022552 A2 | 2/2011 | |
| WO | 2015/159583 A1 | 10/2015 | |

OTHER PUBLICATIONS

University of Rochester Medical Center Health Encyclopedia. retreived from: https://www.urmc.rochester.edu/encyclopedia/content.aspx?contenttypeid=167&contentid=basic_metabolic_panel_blood (Year: 2015).*
International Search Report for International Application No. PCT/EP2020/063409, dated Sep. 10, 2020 (three pages).
Written Opinion of the International Search Authority for International Application No. PCT/EP2020/063409 (five pages).
Canadian Office Action for Application No. CA 3,140,235, mailed Aug. 12, 2022, 4 pages.
Canadian Office Action for Application No. CA 3,140,235, mailed May 27, 2024, 4 pages.
English Translation of Chinese Office Action for International Application No. CA 202080035796.8, Mailed Sep. 30, 2023, 12 pages.
English Translation of Indian Office Action for International Application No. 202117052079, Mailed May 6, 2022, 6 pages.
English Translation of Japanese Decision to Grant a Patent for International Application No. JP 2021-568235, mailed Feb. 10, 2025, 6 pages.
English Translation of Japanese Office Action for International Application No. JP 2021-568235, mailed on Jan. 13, 2023, 8 pages.
English Translation of Korean Office Action for International Application No. KR 10-2021- 7040481, Mailed Dec. 29, 2023, 6 pages.
European Examination Report for International Application No. EP 20726083.7, mailed Jun. 13, 2024, 4 pages.
Tatsumi, "Universal Anticoagulant for Medical Laboratory Use," Thrombus Hemostasis Magazine, 2002, vol. 13 No.2, pp. 158-168.

* cited by examiner

MgSO₄

METHODS FOR DETERMINING BLOOD GAS OR METABOLIC PARAMETERS

This application is a national stage filing under 35 U.S.C. § 371 of International Application No. PCT/EP2020/063409, filed on May 14, 2020, which claims priority to Danish Patent Application No. PA 2019 00579, filed on May 14, 2019. The contents of these applications are each incorporated herein by reference in their entirety.

TECHNICAL FIELD

The present invention relates to the field of diagnostic blood sample analysis.

BACKGROUND OF THE INVENTION

Rapid access to blood tests is a mainstay in the diagnosis and treatment of acute disease. Oxygenation status and acid-base balance are determined by arterial blood gas (BG) analysis and constitute a central part of modern evidence-based treatment algorithms in critical care. Furthermore, devices intended for critical care testing allow for assessment of e.g. electrolytes, renal function (creatinine), inflammation (C-reactive protein) and cardiac biomarkers.

The basic metabolic panel (BMP) is used to check the status of a person's kidneys and their electrolyte and acid/base balance, as well as their blood glucose level—all of which are related to a person's metabolism. It can also be used to monitor hospitalized patients and people with certain known conditions, such as hypertension and hypokalemia.

Further, the count of white blood cells (WBC) is an important biomarker for several diseases and a differential WBC count may differentiate different types of blood cells, such as neutrophils, lymphocytes, monocytes, eosinophils and basophils. Each may e.g. be reported as a percentage. A shift in the percentage may indicate a pathological condition.

Further, platelets (also termed thrombocytes) may be counted as another parameter. Platelets are small fragments of cells that are essential for normal blood clotting. A platelet count may be used to screen for or diagnose various diseases and conditions that can cause problems with clot formation. It may be used as part of the workup of a bleeding disorder, bone marrow disease, or excessive clotting disorder, to name just a few. The test may be used as a monitoring tool for people with underlying conditions or undergoing treatment with drugs known to affect platelets. It may also be used to monitor those being treated for a platelet disorder to determine if therapy is effective.

However, blood samples usually have to be differently prepared for diagnostic measurements of the abovementioned parameters. For example, for BG and BMP parameter analysis, the standard anti-coagulant is heparin. Heparin prevents blood coagulation, but it however does not prevent platelet (thrombocyte) activation and aggregation, which leads to platelet aggregate formation. Heparin is therefore nowadays not used for a complete blood cell count (CBC) analysis, comprising the counts of WBC, platelets, 3-diff or 5-diff, red blood cell (RBC) concentration, hematocrit, hemoglobin concentration and RBC descriptive parameters. The measured platelet count in heparinized blood would be underestimated, in particular when using state of the art automated hematology analyzers, which are not able to distinguish single platelets from aggregated platelet clots. Instead, platelet aggregates may be misclassified by hematological analyzers as leucocytes and therefore, a falsely high WBC count is obtained potentially resulting in a flawed diagnosis or flags and error messages rendering the results unusable.

Ethylenediaminetetraacetic acid (EDTA), either as di-sodium, di-potassium or tri-potassium salt, is another commonly used standard anti-coagulant in hematology. The use of EDTA is generally accepted to be safe and reliable for obtaining complete blood cell counts. In addition, EDTA salts are compatible, i.e. do not interfere, with standard staining protocols for blood smears. If problems with EDTA-dependent pseudothrombocytopenia occur, citrate is used as the alternative anti-coagulant. However, EDTA or citrate cannot be used for BG and BMP parameter analysis as these anti-coagulants strongly interfere with electrolyte measurements. For example, EDTA and citrate form a complex with Ca' and thus interfere with Ca' measurements and these anti-coagulants might even destroy the calcium-sensors of the automated analyzers.

Currently, hematology analysis, and in particular CBC, is performed on EDTA or citrate anti-coagulated blood samples and not on heparinized blood samples.

Consequently, a comprehensive analysis of CBC, BG and BMP parameters so far needs to be performed with separate differently anti-coagulated blood samples on separate instruments.

Schnuff-Wernet et al. (Br. J. Haematol. 162, 684, 2013) describe that $MgSO_4$ may be used as anti-coagulant for blood samples of patients with pseudothrombocytopenia as an alternative to EDTA or citrate.

US 2010/0280412 discloses blood coagulation factor Xa inhibitors and a method for anti-coagulation of human blood in which blood calcium concentration remains the same and no thrombin is formed and thrombocyte function is not affected.

U.S. Pat. No. 6,880,384 B2 describes an automated blood analyzer for measuring blood gas parameters, metabolic parameters and electrolytes as well as a blood sampler containing the blood sample and a stirring element.

WO2019096598 describes an in vitro method for preparing a blood sample, wherein blood is combined with
  a) at least one anti-coagulant for the determination of blood gas and basic metabolic panel parameters; and
  b) at least one anti-platelet agent.

The blood sample prepared according to said method is suitable for BG and BMP parameter analysis as well as platelet count. Thus, all parameters can be determined using the same blood sample and the same automated blood analyzer. WO2019096598 also describes an in vitro method for determining blood gas and BMP parameter and platelet count in a blood sample prepared according to said sample preparation method.

SUMMARY

In a first aspect, the invention relates to an in vitro method for determining a blood gas parameter and/or a basic metabolic panel (BMP) parameter in a blood sample comprising the steps of:
  i) combining a blood sample with an anti-coagulant and an anti-platelet agent, and
  ii) determining said blood gas parameter and/or BMP parameter in the sample, wherein said blood sample, prior to the determination in step ii), has been subjected to pre-analytical stress, such as stress caused by exposure to temperature below 20° C., by contact with air and/or by shear forces.

Similarly, in a second aspect, the invention relates to an in vitro method for determining a blood gas parameter and/or a BMP parameter in a blood sample comprising the steps of:
i) combining a blood sample with an anti-coagulant and an anti-platelet agent,
ii) exposing said blood sample to a temperature below 20° C., and
iii) determining said blood gas parameter and/or BMP parameter in the sample.

In a third aspect, the invention relates to an in vitro method for determining a blood gas parameter selected from the group consisting of $pO_2$ and $pCO_2$ in a blood sample comprising the steps of
i) combining a blood sample with an anti-coagulant and an anti-platelet agent, and
ii) determining said blood gas parameter in the sample,
wherein step ii) is performed in sensor assembly comprising two or more analyte sensors, wherein said two or more analyte sensors are not all positioned in the same plane, and wherein one of said analyte sensors analyzes said blood gas parameter and wherein another analyte sensor not located in the same plane analyzes a different blood gas parameter or a BMP parameter.

DETAILED DESCRIPTION

In a first aspect, the invention relates to an in vitro method for determining a blood gas parameter and/or a basic metabolic panel (BMP) parameter in a blood sample comprising the steps of:
i) combining a blood sample with an anti-coagulant and an anti-platelet agent, and
ii) determining said blood gas parameter and/or BMP parameter in the sample,
wherein said blood sample, prior to the determination in step ii), has been subjected to pre-analytical stress, such as stress caused by exposure to temperature below 20° C., by contact with air and/or by shear forces. Pre-analytical stress when used herein indicates stress subjected to the sample before analysis, i.e. before the determination of parameters in step ii).

Similarly, in a second aspect, the invention relates to an in vitro method for determining a blood gas parameter and/or a BMP parameter in a blood sample comprising the steps of:
i) combining a blood sample with an anti-coagulant and an anti-platelet agent,
ii) exposing said blood sample to a temperature below 20° C., and
iii) determining said blood gas parameter and/or BMP parameter in the sample.

It has surprisingly been found that the presence of both an anti-coagulant and an anti-platelet agent in a blood sample improves the accuracy and robustness of determination of BG and BMP parameters. Thus, even samples that have been subjected to stress due to e.g. low temperature, contact with air or high shear forces can reliably be used for determination of these parameters. The inventors have observed that under such stress conditions, having both an anti-coagulant and an anti-platelet agent present in the sample provided fewer measurement errors due to clots than when only an anti-coagulant was added. Without being bound by any theory, it is believed that the presence of the anti-platelet agent prevents activation of platelets and thus formation of platelet aggregates. Platelet aggregates were not previously known as a source of errors in the determination of BG and BMP parameters. In conclusion, the method of the invention allows for more accurate determination of BG and BMP parameters in samples that have been subjected to stress. In addition, the blood sample prepared according to step i) of the method is suitable for BG and BMP parameter analysis as well as platelet count and thus all parameters can be determined using the same blood sample and the same automated blood analyzer. It is thus a further advantage of the present inventive method that it allows a "3-in-1" analysis with one blood sample.

In a third aspect, the invention relates to an in vitro method for determining a blood gas parameter selected from the group consisting of $pO_2$ and $pCO_2$ in a blood sample comprising the steps of
i) combining a blood sample with an anti-coagulant and an anti-platelet agent, and
ii) determining said blood gas parameter in the sample,
wherein step ii) is performed in sensor assembly comprising two or more analyte sensors, wherein said two or more analyte sensors are not all positioned in the same plane, and wherein one of said analyte sensors analyzes said blood gas parameter and wherein another analyte sensor not located in the same plane analyzes a different blood gas parameter or a BMP parameter. A multisensory assembly in which the sensors are not all on the same plane, e.g. in a sandwich configuration or a tube, allows for analysis of smaller volumes of samples. Again, one advantage of the inventive method is that multiple parameters can be measured from one sample.

Pre-Analytical Stress

As described above, in the method of the invention, a blood sample is combined with an anti-coagulant and an anti-platelet agent before determination of a BG and/or BMP parameter in said sample. Combining the blood sample with an anti-coagulant and an anti-platelet agent renders the sample more robust against pre-analytical stress, such as stress caused by exposure to temperature below 20° C., by contact with air and/or by shear forces.

Stress caused by exposure to temperature below 20° C. can e.g. occur if a sample is stored or incubated on ice. A temperature drop can also occur during handling or transport of a sample prior to analysis. It is understood that exposure must have been of a sufficient minimum time to cause a significant lowering of the temperature of the blood sample itself, so that this indeed has caused stress. In one embodiment, the blood sample has been subjected to stress caused by exposure to temperature between −5° C. and 20° C., such as temperature between −5° C. and 15° C. e.g. temperature between 0° C. and 10° C., such as stress caused by temperature between 0° C. and 5° C. In further embodiments, the blood sample has been subjected to stress caused by exposure to temperature of from −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C. or 19° C. to −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C. or 20° C. In one embodiment, the exposure time has been at least 5 sec, such as at least 10 sec, at least 30 sec, at least 1 min, at least 2 min, at least 5 min, at least 10 min or at least 30 min.

The ability to incubate or store a blood sample at low temperature, e.g. below 10° C., for instance on ice, may be desirable for certain purposes, in particular for the determination of BMP parameters in which an incubation at low temperature prevents further metabolism in the sample during handling prior to analysis.

Stress caused by contact with air can e.g. occur if a sample is handled suboptimally before analysis, for instance if a blood sample is drawn with a syringe and air enters the syringe and is not removed before subsequent steps in the analysis procedure. In particular, mixing of a blood sample in the presence of air can increase such stress. Thus, in one embodiment, the stress caused by contact with air is stress caused by contact with air during mixing of the sample. Accordingly, in one embodiment, the method of the invention includes a mixing step prior to the determination wherein the sample is in contact with air during the mixing step.

Stress caused by shear forces can occur in several ways, e.g. if a sample is subjected to average shear rates above 10000 s−1 for a period of time, such as a period of more than 0.1 sec, more than 0.2 sec more than 0.5 sec, more than 1 sec, more than 2 sec or more than 5 sec. Shear rates above 10000 s−1 have been described as "pathological" because they can lead to the formation of large rolling aggregates (Nesbitt et al. (2009) Nature Medicine 15: 665; Ruggeri et al. (2006) Blood 108:1903). Average shear rates can e.g. be determined using simulation techniques. For example, COMSOL Multiphysics (v. 5.2. www.comsol.com. COMSOL AB, Stockholm, Sweden) is a commercially available software known for its ability to solve physics based problems. In another embodiment, sample has been subjected to average shear rates above 12000 s−1, above 15000 s−1 or above 20000 s−1 for a period of time, such as a period of more than 0.1 sec, more than 0.2 sec, more than 0.5 sec, more than 1 sec, more than 2 sec or more than 5 sec. Stress caused by shear forces can also occur if a sample is handled suboptimally before analysis, for instance if a sample is subjected to vigorous shaking or vortexing (as opposed to mixing, which is a gently procedure that does not cause stress). Furthermore, stress caused by shear forces can also occur during automated handling or transport of samples during the procedure. Automated sample management systems may e.g. cause samples to bump onto a surface or into a sample receiving device. In one embodiment of the method of the invention, the blood sample is handled in an automated system (i.e. without manual handling by a human being) in all steps subsequent to drawing of the blood, or all steps subsequent to step i) of the method.

Parameters

As described above, the invention relates to in vitro methods for determining a BG parameter and/or a BMP parameter.

In a preferred embodiment, the method is for determining a BG parameter. In a further embodiment, the blood gas parameter is selected from the group consisting of: pH, $pCO_2$, $pO_2$, oxygen saturation ($sO_2$), the concentration of total hemoglobin (ctHb), the fraction of oxyhemoglobin ($FO_2Hb$), the fraction of carboxyhemoglobin (FCOHb), the fraction of methemoglobin (FMetHb), the fraction of deoxyhemoglobin (FHHb) and the fraction of fetalhemoglobin (FHbF). In a preferred embodiment, the blood gas parameter is $pO_2$ or $pCO_2$.

In another embodiment, the method is for determining pH and the blood sample, has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining $pCO_2$ and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining $pO_2$ and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining sO2 and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining ctHb and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining $FO_2Hb$ and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining FCOHb and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining FMetHb and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining FHHb and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining FHbF and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8°

C., or below 7° C., or below 6° C., or below 5° C., or below 4° C., or below 3° C., or below 2° C., or below 1° C.

In another embodiment, the method is for determining a BMP parameter. In a further embodiment, the BMP parameter is selected from the group consisting of: $Na^+$, $K^+$, $Mg^{2+}$, $Cl^-$, $HCO_3^-$, urea, creatinine, glucose, $Ca^{2+}$, lactate and total bilirubin.

In another embodiment, the method is for determining $Na^+$ and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining $K^+$ and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining $Mg^{2+}$ and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining $Cl^-$ and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining $HCO_3^-$ and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining urea and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining creatinine and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining glucose and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining $Ca^{2+}$ and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining lactate and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C. In another embodiment, the method is for determining total bilirubin and the blood sample has been subjected to stress caused by exposure to temperature below 20° C. or below 19° C., or below 18° C., or below 17° C., or below 16° C., or below 15° C., or below 14° C., or below 13° C., or below 12° C., or below 11° C., or below 10° C., or below 9° C., or below 8° C., or below 7° C., or below 6° C., or below 5° C., or below 4° C., or below 3° C., or below 2° C., or below 1° C.

The method may, or may not, further comprise determining platelet count and/or white blood cell count in the sample obtained in step i). In one embodiment, the white blood cell count is a total white blood cell count. In another embodiment, the white blood cell count is a count of five different types of blood cells ("5-diff" or "5-part diff"), namely neutrophils, lymphocytes, monocytes, eosinophils and basophils, or a count of one, two or more of these types. In some embodiments, neutrophils, basophils and eosinophils are reported as a group as granulocytes. Each may e.g. be reported as a percentage. A shift in the percentage may indicate a pathological condition.

In one embodiment, the method is for determining two or more of the above-mentioned parameters in the same sample, such as three or more, four or more, five or more, six or more, eight or more, ten or more, twelve or more, fourteen or more, sixteen or more, eighteen or more or nineteen or more of the above-mentioned parameters in the same sample, e.g. determining these parameters simultaneously in the same sample.

In one embodiment, the method is for determining two or more of the above-mentioned parameters in the same sample, wherein said two or more parameters include:
pH and $K^+$ or
$pO_2$ and $K^+$ or
$pCO_2$ and $K^+$ or
pH and glucose or
$pO_2$ and glucose or
$pCO_2$ and glucose.

Sensor Assemblies

In principle any suitable method may be used for the step of determining said blood gas parameter and/or BMP parameter in the sample.

In one embodiment, the determination is performed in a sensor assembly using one or more analyte sensors. Preferably, the determination is performed in a sensor assembly comprising two or more analyte sensors, thus facilitating simultaneous determination of two or more parameters.

Advantageously, said two or more analyte sensors are not all positioned in the same plane, and one of said analyte sensors analyzes said blood gas parameter or said BMP parameter, and another analyte sensor not located in the same plane analyzes a different blood gas parameter or BMP parameter. A multisensory assembly in which the sensors are not all on the same plane, e.g. in a sandwich configuration or a tube, allows for analysis of smaller volumes of samples. The term "plane" when used herein means a flat two-dimensional surface. In one preferred embodiment, said two or more analyte sensors are located on two or more planes which are not positioned at an angle of 180° relative to each other. In another preferred embodiment, said two or more analyte sensors are not all positioned at an angle of 180° relative to each other.

In a preferred embodiment, the determination is performed in a sensor assembly comprising:
a) a first electronic wiring substrate having a first and a second surface and at least one analyte sensor formed on the first surface thereof, the at least one analyte sensor being connected with one or more electrical contact points,
b) a second electronic wiring substrate having a first and a second surface and at least one analyte sensor formed on the first surface part thereof, the at least one analyte sensor being connected with one or more electrical contact points, and
c) a spacer having a through-going recess with a first and a second opening, wherein the first substrate, the second substrate and the spacer are arranged in a layered structure, where the first surface of the first substrate closes the first opening of the spacer and the first surface of the second substrate closes the second opening of the spacer, thereby forming a measuring cell which is faced by at least one analyte sensor from each of the substrates. Such sensor assemblies have been described in WO2008/131767 (Radiometer Medical ApS). In a further embodiment hereof, the volume of the measuring cell is less than 1 ml, such as less than 0.5 ml, e.g. less than 200 microliter, such as less than 100 microliter, e.g. less than 50 microliter, such as less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter. In a further embodiment, the volume of the measuring cell is between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter. Thus, in one embodiment, the volume used for the determination, i.e. the volume contained within the measuring cell, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter. The measuring cell provided by the recess in the spacer and the first surfaces of the first and second substrates preferably provides a volume of about 25-45 microliter, more preferably a volume of about 30-40 microliter. With such a volume very small samples are required for measurement by the analyte sensors in the measuring cell. Preferably the dimensions of the spacer are within the ranges: length 20-60 mm, width 5-20 mm, and thickness 0.2-0.6 mm. The recess within the spacer may have the dimensions within the ranges: length 10-50 mm, width 1-5 mm, and depth 0.2-0.6 mm. The dimensions of the first and second substrates and the spacer, and thus, the dimension of the sensor assembly may be adapted depending on the intended use. However, in a preferred embodiment the first substrate has dimensions within the ranges: length about 20-60 mm, width about 5-20 mm, and thickness about 0.3-0.8 mm. The width and/or the length of the second substrate may be somewhat larger than the width and/or length of the first substrate. This is due to the fact that for some preferred embodiments it is preferred that the first surface of the second substrate projects over the edges of the spacer and first substrate in the sensor assembly. The second substrate preferably has dimensions within the ranges: length about 20-60 mm, width about 5-40 mm, and thickness 0.3-0.8 mm. The length and width of the second substrate may provide an extension beyond the edges of the first substrate and spacer in the range of about 4-20 mm.

In another embodiment, the determination is performed in a sensor array comprising: a housing having a base, a top spaced above the base, and an outer wall that extends from the base to the top; an inlet in the housing that is sized to receive a sample of the fluid; a plurality of partitions arranged around the fluid inlet and substantially isolated from each other, each partition having a port at the fluid inlet for receiving a portion of the sample of fluid received by the fluid inlet; and at least one sensor in each partition, wherein the at least one sensor is responsive to the fluid when the fluid contacts the at least one sensor, wherein the sensor array is configured to selectively direct the sample of fluid received by the one or more of the plurality of partitions from the fluid inlet into contact with the at least one sensor. Such sensor arrays have been described in WO 2018/112017. In a further embodiment hereof, the volume used for the determination in each partition, i.e. the volume contained within the partition, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the determination is performed in a sensor assembly comprising: a first microsensor having a first outer sheath, a first membrane core within the first outer sheath, and a first conductive element that is at least partially encased by and in contact with the first membrane core, wherein the first conductive element detects a first electrical response signal when the first membrane core is in contact with a fluid; and a second microsensor adjacent to the outer surface of the first microsensor, the second microsensor having a second outer sheath, a second membrane core within the second outer sheath, and a second conductive element that is at least partially encased by and in contact with the second membrane core, wherein the second conductive element detects a second electrical response signal when the second membrane core is in contact with the fluid. Such sensor assemblies have been described in WO 2018/112012. In a further embodiment hereof, the volume used for the determination, i.e. the volume contained within the measuring cell, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the determination is performed in a microcapillary sensor array, comprising: a sensor body elongated along a longitudinal axis, the sensor body having a first end, a second end spaced from the first end along the longitudinal axis, an outer surface, and an inner surface, wherein the inner surface defines a hollow capillary that extends from the first end toward the second end along the longitudinal axis; a sensing element that extends through the sensor body from the outer surface to the hollow capillary; and a conductive element in contact with the sensing element; wherein the conductive element detects a response signal generated by a reaction between the sensing element and a fluid as the fluid flows through the hollow capillary contacting the sensing element. Such sensor arrays have been described in WO 2018/112008. In a further embodiment hereof, the volume used for the determination, i.e. the volume contained within the measuring cell, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the determination is performed in a test device comprising: a first planar substrate with a first planar surface; a second planar substrate with a second planar surface; a first sensing area and a second sensing area, the first sensing area and the second sensing area being disposed in between the first planar surface and the second planar surface, both of the first sensing area and the second sensing area comprising a chemical and/or reagent in electrical connection with a first electrode and a second electrode, respectively; a first planar intermediate isolating layer with a flow channel, wherein the first sensing area opposes the second sensing area with the flow channel disposed in between the first sensing area and the second sensing area; and a first heating element disposed in between the first planar surface and the second planar surface. Such test devices have been described in WO 2017/120464. In a further embodiment hereof, the volume used for the determination, i.e. the volume contained within the measuring cell, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the determination is performed in a test device comprising: a first planar intermediate isolating layer with at least a first sensing area; a second planar intermediate isolating layer with at least a second sensing area; a third planar intermediate isolating layer with a flow channel 14, wherein the first sensing area opposes the second sensing area with the flow channel disposed in between the first sensing area and the second sensing area; a first planar conductive layer disposed adjacent to the first intermediate isolating layer opposite the third planar intermediate isolating layer; a first planar substrate disposed adjacent to the first planar conductive layer opposite the first intermediate isolating layer; a second planar substrate disposed adjacent to the second planar intermediate isolating layer opposite the third planar intermediate isolating layer, the second planar substrate having at least a first conductive via in electrical contact with the second sensing area; and a second planar conductive layer disposed adjacent to the second planar substrate opposite the second planar intermediate isolating layer, the second planar conductive layer being in electrical contact with first conductive via, wherein each of the first planar intermediate isolating layer, the second planar intermediate isolating layer, the third planar intermediate isolating layer, first planar conductive layer, the first planar substrate, the second planar substrate, and the second planar conductive layer have two planar surfaces separated by a thickness, each of the respective two planar surface having an planar area that is approximately equal, wherein the planar area of first conductive layer is greater than the planar area of each of the first planar intermediate isolating layer, the second planar intermediate isolating layer, the third planar intermediate isolating layer, the second planar substrate, and the second planar conductive layer. Such test devices have been described in WO 2017/019609. In a further embodiment hereof, the volume used for the determination, i.e. the volume contained within the measuring cell, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the determination is performed in a test device comprising: a single substrate, the substrate having a first surface, the first surface having a first area and a second area separated by a line, the first area opposing the second area of the first surface of the single substrate; a conductor layer disposed on the single substrate, the conductor layer comprising a first group of electrodes printed in the first area and a second group of electrodes printed in the second area; a dielectric layer disposed on the conductor layer, the dielectric layer comprising a first area of dielectric material disposed on the first group of electrodes and a second area of dielectric material disposed on the second group of electrodes, the first area of dielectric material and the second area of dielectric material each comprising a respective first group and a second group of reaction wells formed in the dielectric layer, at least one reaction well being electrically coupled to a respective electrode and containing chemistries; and a spacer layer adjacent to the first area of dielectric material and the second area of dielectric material, the spacer layer forming a flow path between the first group and the second group of reaction wells. Such test devices have been described in WO 2016/106320. In a further embodiment hereof, the volume used for the determination, i.e. the volume contained within the measuring cell, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the determination is performed in a test strip comprising: a first planar substrate with coplanar electrodes on a first planar surface and a second planar substrate with coplanar electrodes on a second planar surface, the first planar substrate and the second planar substrate being arranged such that the first surface of the first planar substrate opposes the second planar surface of the second planar substrate; an intermediate layer disposed in between the opposed first surface of the first planar substrate and the second planar surface of the second planar substrate; the first planar surface of the first planar substrate having a first sensing area electrically connected to a first electrical contact; and the second planar surface of the second planar substrate having a second electrical contact electrically connected to the first electrical contact via a conductive element, the conductive element extending between the first surface of the first planar substrate and the second surface of the second planar substrate without passing through the first planar substrate or the second planar substrate. Such test strips have been described in WO 2016/011308 In a further embodiment hereof, the volume used for the determination, i.e. the volume contained within the measuring cell, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the determination is performed in a sensor assembly comprising: a first planar substrate having a base layer, a conductive layer formed on a first planar surface of the base layer, and an dielectric layer formed on at least one of a first planar surface of the conductive layer or the first planar surface of the base layer, the dielectric layer having a first planar surface located a distance from the first planar surface of the conductive layer, the conductive layer comprising at least at least a first electrical contact and a second electrical contact electrically isolated from the first electrical contact, the dielectric layer defining a liquid flow path through the dielectric layer, the flow path having two side walls and a bottom surface extending between the two side walls, the two side walls extending between the first planar surface of the base layer and the first planar surface of the dielectric layer, and the dielectric layer further defining a first sensing area and a second sensing area above the respective first electrical contact and the second electrical contact of the conductive layer, the first sensing area and the second sensing area allowing liquid in the flow path to contact the first electrical contact and the second electrical contact, respectively; and a second planar substrate, the second substrate being bonded to the first substrate, when bonded to the first substrate the second substrate defining a upper surface of the liquid flow path, the upper surface of the liquid flow path extending between the two side walls and located at a distance from the bottom surface of the flow path. Such sensor assemblies have been described in WO 2016/007716. In a further embodiment hereof, the volume used for the determination, i.e. the volume contained within the measuring cell, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the determination is performed in a sensor assembly, comprising: a substrate having a first surface and a second surface opposite the first surface; at least one analyte sensor positioned on at least one of the first surface and the second surface of the substrate; and at least one electrical contact positioned on the substrate in electrical communication with a corresponding one of the at least one analyte sensor, wherein the substrate is configured to define a tube having an interior surface, and an exterior surface with at least a portion of the first surface of the substrate defining the interior surface of the tube and the at least one analyte sensor disposed on at least one of the interior surface and the exterior surface of the tube. Such sensor assemblies have been described in WO 2013/163120. In a further embodiment hereof, the volume used for the determination, i.e. the volume contained within the measuring cell, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In a preferred embodiment, the determination of BG and BMP parameters as well as the platelet count is performed with an automated blood analyzer. Suitable blood analyzers are for example described in U.S. Pat. No. 5,564,419 or 6,880,384.

Samples

The blood sample is typically whole blood. In a preferred embodiment, the blood of the blood sample is not a purified fraction of a specific type of blood cells, e.g. not a preparation or population of platelets, such as a population of washed platelets.

In some embodiments, all steps of the method are performed on whole blood, i.e. step i) (combination with an anti-coagulant and an anti-platelet agent) is performed on whole blood, the blood sample subjected to pre-analytical stress is the whole blood sample and step ii) (determining the parameter(s)) is performed on whole blood.

In other embodiments, step i) is performed on whole blood, the blood sample subjected to pre-analytical stress is the whole blood sample and step ii) is performed on a blood fraction, such as serum or plasma.

In even further embodiments, step i) is performed on whole blood, the blood is then fractionated, e.g. into a serum or plasma sample, and the fractionated sample, e.g. serum or plasma sample, is subjected to pre-analytical stress prior to the determination in step ii).

The blood may either be venous blood or arterial blood. It is preferred that the blood is arterial blood. However, the use of venous blood may be preferred when the inventive method is used for preparing blood samples in the setting of an emergency department. In one embodiment, the blood may be capillary blood. This embodiment is especially preferred if the blood sample is obtained from neonates.

Anti-Coagulants and Anti-Platelet Agents

As described above, the methods of the invention comprise combining a blood sample with an anti-coagulant and an anti-platelet agent. The terms "a" or "an" wherein used herein have the meaning "at least one", unless specified otherwise.

Thus, the blood sample can be combined with more than one anti-coagulant and/or more than one anti-platelet agent. It is understood that the anti-coagulant used in the method of the invention is an anti-coagulant suitable for the determination of BG and BMP parameters, i.e. a substance that is suitable as anti-coagulant in a blood sample so that the blood sample can be used for the analysis of BG and BMP parameters.

In a preferred embodiment, is selected from the group consisting of indirect factor Xa inhibitors or direct factor Xa inhibitors or combinations thereof.

In a preferred embodiment, the anti-coagulant is selected from the group of heparinates or heparinoids or combinations thereof. Preferred embodiments of heparinates are heparin, such as unfractionated, high molecular weight heparin (HMWH), low molecular weight heparin (LMWH) including bemiparin, certoparin, dalteparin, enoxaparin, nadroparin, parnaparin, reviparin, tinzaparin; and oligosaccharides such as fondaparinux, idraparinux. Preferred embodiments of heparinoids comprise danaparoid, dermatan sulfate and sulodexide.

Preferred embodiments of direct factor Xa inhibitors comprise apixaban, betrixaban, darexaban, edoxaban, otamixaban and rivaroxaban.

In a preferred embodiment, the anti-coagulant suitable for BG and BMP parameter analysis comprises heparin. As described above, heparin is the standard anti-coagulant for BG and BMP parameter analysis. Heparin is a naturally occurring polysaccharide that inhibits coagulation, the process that leads to thrombosis. Natural heparin consists of molecular chains of varying lengths, or molecular weights. It is also used as an anti-coagulant medication (blood thinner). It binds to the enzyme inhibitor antithrombin III (AT), causing a conformational change that results in its activation through an increase in the flexibility of its reactive site loop. The activated AT then inactivates thrombin, factor Xa and other proteases.

In a preferred embodiment, the anti-coagulant is electrolyte-balanced heparin, (also called "balanced heparin"). Heparin is known to bind positively charged electrolytes and this may interfere with electrolyte measurements. It is preferred that the formulations of electrolyte-balanced heparin comprise lithium, zinc, sodium, potassium or ammonium salts of heparin. In a preferred embodiment, the formulation of electrolyte-balanced heparin comprises lithium heparin and sodium heparin.

In another embodiment, the anti-coagulant heparin is human heparin, pig heparin or synthetic heparin. In a preferred embodiment, the anti-coagulant is pig heparin. In another preferred embodiment, the anti-coagulant is unfractionated heparin.

In a preferred embodiment, the final concentration of the anti-coagulant, e.g. heparin, is from about 10 IU/mL to about 200 IU/mL, preferably from about 20 IU/mL to about 100 IU/mL. In a particularly preferred embodiment, the final concentration of the anti-coagulant, e.g. heparin, is about 60 IU/mL.

In one embodiment, the anti-coagulant used according to the present invention can be in a liquid form, also called "liquid heparin", or in a dry form, e.g. as dry balanced heparin when combined with the blood. One example of a dry form of the anti-coagulant is a lyophilized anti-coagulant, e.g. lyophilized heparin or lyophilized balanced heparin.

In one embodiment, the anti-coagulant is in lyophilized form when combined with the blood.

In a preferred embodiment, the anti-platelet agent is selected from the group consisting of glycoprotein IIb/IIIa inhibitors, ADP receptors/P2Y$_{12}$ inhibitors, prostaglandin analogs, COX inhibitors, thromboxane inhibitors, phosphodiesterase inhibitors, cloricromen, ditazole, vorapraxar or combinations thereof.

Glycoprotein IIb/IIIa, also known as integrin αIIbβ3, is an integrin complex found on platelets. It is a receptor for fibrinogen and von Willebrand factor and aids platelet activation. Glycoprotein IIb/IIIa inhibitors can be used to prevent blood clots in an effort to decrease the risk of heart attack or stroke. Examples of glycoprotein IIb/IIIa include, but are not limited to abciximab, eptifibatide (also called integrillin), orbofiban, lotrafiban, roxifiban, sibrafiban and tirofiban (also called aggrastat) or a salt thereof. Preferred glycoprotein IIb/IIIa inhibitors are eptifibatide and tirofiban or a salt thereof.

Adenosine diphosphate (ADP) receptor/P2Y$_{12}$ inhibitors are a drug class of anti-platelet agents, used in the treatment of acute coronary syndrome or as a prevention in patients who are in risk of thromboembolism, myocardial infarction or a stroke. The mechanism of action consists in antagonizing the P2Y$_{12}$ protein and therefore prevent the binding of ADP to the P2Y$_{12}$ receptor. This leads to a decrease in aggregation of platelets, prohibiting thrombus formation. The P2Y$_{12}$ receptor is a surface bound protein found on blood platelets. They belong to G protein-coupled purinergic receptors (GPCR) and are chemoreceptors for ADP. Examples of ADP receptors/P2Y$_{12}$ inhibitors include, but are not limited to thienopyridines such as clopidogrel, prasugrel and ticlopidine or a salt thereof; and nucleotide/nucleoside analogs/receptor antagonists such as cangrelor, elinogrel, ticagrelor, suramin sodium and 2-MeSAMP. The thienopyridines are less preferred ADP receptors/P2Y$_{12}$ inhibitors according to the present invention as they are prodrugs that do not show ADP receptors/P2Y$_{12}$ inhibitory activity in vitro. Consequently, nucleotide/nucleoside analogs/receptor antagonists such as cangrelor, elinogrel, ticagrelor or a salt thereof, suramin sodium and 2-MeSAMP are preferred ADP receptors/P2Y$_{12}$ inhibitors according to the present invention.

Prostaglandins may induce or inhibit platelet aggregation and constrict to dilate blood vessels. Prostaglandin analogs are a class of drugs that bind to a prostaglandin receptor. Examples include but are not limited to beraprost, iloprost (also known as ZK36374), prostacyclin, epoprostenol, and treprostinil.

Cyclooxygenase (COX), officially known as prostaglandin-endoperoxide synthase (PTGS), is an enzyme that is responsible for formation of prostanoids, including thromboxanes and prostaglandins. Examples of COX inhibitors include, but are not limited to acetlysalicylic acid, aloxiprin, carbasalate calcium, ibuprofen, trifusal, sulfinpyrazone and nitroaspirin (NCX-4016).

Thromboxane is a member of the family of lipids known as eicosanoids. The two major thromboxanes are thromboxane A2 and thromboxane B2. The distinguishing feature of thromboxanes is a 6-membered ether-containing ring. Thromboxane is named for its role in clot formation. Thromboxane-A synthase, an enzyme found in platelets, converts the arachidonic acid derivative prostaglandin H2 to thromboxane. Thromboxane inhibitors comprise thromboxane synthase inhibitors such as dtritriipyridamole, picotamide, terbogrel, daltrob an, seratrodast, SQ-29548 and ramatroban; and thromboxane receptor antagonists such as terbogrel and terutroban.

A phosphodiesterase is an enzyme that breaks a phosphodiester bond. Phosphodiesterase enzymes (PDE) are often targets for pharmacological inhibition due to their unique tissue distribution, structural properties, and functional properties. Inhibitors of phosphodiesterases can prolong or enhance the effects of physiological processes mediated by cAMP or cGMP by inhibition of their degradation by phosphodiesterases. PDE inhibitors have been identified as new potential therapeutics in areas such as pulmonary arterial hypertension, coronary heart disease, dementia, depression, asthma, COPD, protozoal infections, including malaria, and schizophrenia. Further, cyclic adenosine 3',5'-monophosphate (cAMP) and cyclic guanosine 3',5'-monophosphate (cGMP) are two critical intracellular second messengers provided with strong inhibitory activity on fundamental platelet functions. PDEs, by catalysing the hydrolysis of cAMP and cGMP, limit the intracellular levels of cyclic nucleotides, thus regulating platelet function. The inhibition of PDEs may therefore exert a strong platelet inhibitory effect (Gresele et al. Br. J. Clin. Pharmacol. 2011 October; 72(4):634-46). Examples of PDEs include, but are not limited to Cilostazol, Dipyridamole, Trifusal, Milrinone, Anagrelide and Theophylline.

Anti-platelet drugs which are not known to belong one of the above groups include, but are not limited to cloricromen, ditazole, vorapraxar and L-Arginine or salts thereof.

Cloricromen is an anti-platelet drug with vasodilating activity that is used in the treatment of thromboembolic disorders.

Ditazole is a non-steroidal anti-inflammatory agent with analgesic and antipyretic activity similar to phenylbutazone. Additionally, ditazole is a platelet aggregation inhibitor marketed in Spain and Portugal with trade name Ageroplas®.

Vorapraxar, formerly known as SCH 530348, is a thrombin receptor (protease-activated receptor, PAR-1) antagonist based on the natural product himbacine.

It has been shown that oral L-Arginine inhibits platelet aggregation by way of the nitric oxide pathway (Adams et al., J. Am. Coll. Cardiol. 1995 October; 26(4):1054-61).

It is preferred that the anti-platelet agent is selected from the group consisting of glycoprotein IIb/IIIa inhibitors, ADP receptors/$P2Y_{12}$ inhibitors, prostaglandin analogs, cloricromen, ditazole, vorapraxar or combinations thereof.

In another preferred embodiment, the anti-platelet agent is selected from the group consisting of glycoprotein IIb/IIIa inhibitors, prostaglandin analogs, cloricromen, ditazole, vorapraxar or combinations thereof.

In another preferred embodiment, the anti-platelet agent is selected from the group consisting of glycoprotein IIb/IIIa inhibitors and prostaglandin analogs.

In a preferred embodiment, the anti-platelet agent comprises a prostaglandin analog.

In yet another preferred embodiment, the anti-platelet agent is a glycoprotein IIb/IIIa inhibitor selected from the group consisting of abciximab, eptifibatide, orbofiban, lotrafiban, roxifiban, sibrafiban and tirofiban or a salt thereof. In a preferred embodiment, the anti-platelet agent comprises eptifibatide and/or tirofiban or a salt thereof. In a preferred embodiment eptifibatide is used as the eptifibatide acetate salt. It is also preferred that tirofiban is used as the tirofiban hydrochloride salt and more preferably the tirofiban hydrochloride monohydrate salt.

In yet another preferred embodiment, the anti-platelet agent is a prostaglandin analog selected from the group consisting of beraprost, iloprost, prostacyclin, epoprostenol, treprostinil or a salt thereof.

In a particularly preferred embodiment, the anti-platelet agent comprises eptifibatide, tirofiban, iloprost, a salt thereof or a combination thereof.

It is especially preferred that the antiplatelet agent comprises iloprost. Iloprost is particularly preferred as the anti-platelet agent as it is not only suitable for the preparing of a blood sample for BG, BMP and platelet count but it was also surprisingly found that it inhibits leukocyte activation and thus a very low WBC aggregation in the blood sample.

In another embodiment, antiplatelet agent comprises ADP receptors/$P2Y_{12}$ inhibitors, wherein the ADP receptors/$P2Y_{12}$ inhibitors is a nucleotide/nucleoside analog/receptor antagonist. It is preferred that the ADP receptors/$P2Y_{12}$ inhibitors is selected from the group consisting of cangrelor, elinogrel, ticagrelor or a salt thereof, suramin sodium, 2-MeSAMP.

In another preferred embodiment, the inventive method does not comprise the step of combining $MgSO_4$, EDTA or citrate with the blood of the blood sample. These anticoagulant agents are not suitable for preparing a blood sample for BG and BMP parameter analysis.

In one embodiment of the method of the invention, the sample has been subjected to pre-analytical stress after step i), i.e. after the sample was combined with an anti-coagulant and an anti-platelet agent.

In another preferred embodiment, the inventive method further comprises the step of mixing the blood sample. The mixing of the blood sample is advantageous as the blood sample may otherwise coagulate or settle or the sample may react with air in the blood samples prior to analysis. The mixing may for example occur by stirring. The mixing may be performed manually by repeatedly inverting the blood sample or by rolling it horizontally. A stirring element may also be included to the blood sample. The sample may then for example be stirred by using moving means, e.g. as described in U.S. Pat. No. 6,880,384 B2. The mixing of the blood sample facilitates the dissolution of anti-coagulant, e.g. heparin, and it prevents settling. If the anti-coagulant is not properly dissolved, it may lead to formation of micro clots, which may bias the results and/or damage the analyzer. Settling may lead to sample inhomogeneity and misleading analytical results.

In one embodiment, the method of the invention comprises use of a blood sampler containing
 a) anti-coagulant agent as described above; and
 b) anti-platelet agent as described above.

The blood sampler may be used for performing the inventive method described above. The anti-coagulant agent for BG and BMP parameter analysis may be present in a liquid form within the blood sampler or it may be present in a dry formulation.

In one embodiment, the blood sampler contains a further element comprising the anti-coagulant and/or anti-platelet agent. For example, the further element may be a "brick" as it is known for "heparin bricks". A "brick" in this context means that the anti-coagulant was prepared in a "puff" of inert filler material, wherein the puff dissolves and the heparin is dispersed throughout the sample with proper mixing and wherein the puff could be dispensed during production to deliver a reproducible amount of heparin in each sampler. One example of such a brick is e.g. a piece of cellulose soaked with anti-coagulant and/or anti-platelet agent. However, also other further elements that may release the anti-coagulant and/or anti-platelet agent upon contact with blood are possible, e.g. a blood sampler wall coating matrix sprayed on internal sampler surface.

In one embodiment, the blood sampler is comprised of plastic or glass.

In another preferred embodiment, the blood sampler comprises a sampler cap. A sampler cap is a cap to be connected to the open end of a blood sampler, e.g. to the tip of a syringe or to the open end of a capillary tube or a test tube. Gas exchange with the surroundings which may bias the BG analysis results may be avoided by using a sampler cap. Suitable sampler caps are for example described in WO 2004/000412.

In another preferred embodiment, the blood sampler contains a stirring element. It is preferred that the stirring element is a spherical element or a cylindrical element with rounded ends. It is particularly preferred that the stirring element has the form of a ball. The ball may for example be made of steel or plastics.

In another embodiment, the stirring element comprises a coating with an inert material. The inert material does preferably not interfere or not substantially interfere with the blood analysis. For example, the inert material may be selected from the group consisting of gold, platinum, palladium or rhodium. In a preferred embodiment, the inert material is gold.

It is a particularly preferred embodiment that the stirring element is a gold coated ball, preferably a gold coated steel ball.

In one embodiment, the stirring element is a stirring element as described in U.S. Pat. No. 6,880,384 B2. The movement of the stirring element is also described in U.S. Pat. No. 6,880,384 B2. It is thus preferred that the stirring element is moved by moving means, e.g. by mechanical means. The moving means may be a robot arm or a support for moving, e.g. tilting or rotating, the sample handler and/or the sampler bed, thereby moving the stirring element held in any sampler therein by means of gravitational forces.

Definitions

As used herein, the term "parameter" means any piece of clinical information about the blood sample.

As used herein, the term "blood gas" as in "blood gas parameter" refers to gaseous parameters of the blood and includes the amounts of certain gases (e.g. oxygen and carbon dioxide) dissolved in blood, typically arterial blood. Blood gas parameters include the pH, $pCO_2$, $pO_2$, oxygen saturation ($sO_2$), the concentration of total hemoglobin (ctHb or tHb), the fraction of oxyhemoglobin ($FO_2Hb$ or $O_2Hb$), the fraction of carboxyhemoglobin (FCOHb or COHb), the fraction of methemoglobin (FMetHb or MetHb), the fraction of deoxyhemoglobin (FHHb or RHb), and the fraction of fetalhemoglobin (FHbF). A "blood sample suitable for blood gas analysis" means that the blood sample may be used for measuring at least one blood gas parameter but is preferably suitable to measure all blood gas parameters of pH, $pCO_2$, $pO_2$, ctHb, $FO_2Hb$, FCOHb, FMetHb, FHHb, and FHbF. It may be preferred that at least pH, tHb, FCOHb, and FMetHb can be measured.

As used herein, the term "basic metabolic panel" as in "basic metabolic panel parameter analysis" refers to biochemical blood parameters, in particular electrolytes, namely the concentration of $Na^+$, $K^+$, $Mg^{2+}$, $Cl^-$, $HCO_3^-$, urea, creatinine, glucose (glu), $Ca^{2+}$, lactate (lac) and total bilirubin (tBil). A "blood sample suitable for BMP parameter analysis" is thus a blood sample that can be used to determine at least one but preferably all of the above BMP parameters. It may be preferred that at least $Na^+$, $K^+$, $Mg^{2+}$, $Cl^-$, $Ca^{2+}$, glu, lac and tBil can be measured.

As used herein, the term "platelet count" or "determining the number of platelets" means a diagnostic test that determines the number of platelets in the patient's blood. Platelets, which are also called thrombocytes, are small disk-shaped blood cells produced in the bone marrow and involved in the process of blood clotting. There are normally between 150,000-450,000 platelets in each microliter of blood. Low platelet counts or abnormally shaped platelets are associated with bleeding disorders. High platelet counts sometimes indicate disorders of the bone marrow.

As used herein, the term "anti-coagulant" means a substance that prevents or reduces the coagulation of blood, i.e. the coagulation cascade leading to fibrin polymerization and therefore fibrin clot formation. Anti-coagulants thereby prolong the clotting time by inhibiting the coagulation cascade by clotting factors after the initial platelet aggregation.

As used herein, the term "anti-coagulant suitable for the determination of BG and BMP parameters" means that a substance is suitable as anti-coagulant in a blood sample so that the blood sample can be used for the analysis of BG and BMP parameters. Some anti-coagulants, e.g. EDTA, are known to be unsuitable for the determination of BG and BMP parameters, e.g. because they form a complex with $Ca^{2+}$ so that the calcium concentration cannot be reliably determined in a blood sample. Thus, EDTA is not an anti-coagulant suitable for the determination of BG and BMP parameters.

As used herein, the term "anti-platelet agent" means a substance that decreases platelet aggregation and/or inhibits thrombus formation, i.e. a substance that inhibits the initial platelet aggregation of the blood clotting. Anti-platelet agents thus interfere with the platelet activation cascade leading to activated platelets which can adhere to fibrin fibers, other extracellular matrix components or aggregate into platelet aggregates. It is emphasized that the coagulation cascade and the platelet aggregation cascade are two separate cascades, even though some proteins, such as thrombin, may play a role in both cascades. Antiplatelet drugs can reversibly or irreversibly inhibit the process involved in platelet activation resulting in decreased tendency of platelets to adhere to one another and to damaged blood vessels endothelium or to foreign material surfaces, as e.g. a blood sampler material.

As used herein, the term "blood sample" or "blood analysis sample" refers to a sample of blood that is suitable for diagnostic or analytical purposes. Thus, the blood sample comprises a relatively low volume of blood (from 20 µL to 10 mL blood), i.e. not the volumes e.g. required for blood donations (up to about 450 mL blood).

As used herein, the term "blood sampler" means a device for collection of blood, such as a syringe, a capillary tube, or a test tube, e.g. an aspirating sampler or self-aspirating sampler, such as a PICO syringe (Radiometer Medical ApS), a vacuum test tube or a similar device designated for blood sampling.

As used herein, the term "white blood cell count" means a diagnostic test counting the number of leukocytes in a sample of the patient's blood. An average normal range is between 3,500 and 10,500 white blood cells per µL blood.

In general, the present invention preferably includes all salts of the disclosed reagents such as the anti-platelet agent or the anti-coagulant, provided that these salts do not interfere or not substantially interfere with the blood analysis. Examples of salts include inorganic and organic acid addition salts and basic salts. The salts include, but are not limited to, metal salts such as cesium salt, alkaline salts such as lithium salt, sodium salt, potassium salt, calcium salt or magnesium salt, organic amine salts such as triethylamine salt, pyridine salt, picoline salt, ethanolamine salt, triethanolamine salt, dicyclohexylamine salt, N,N'dibenzylethylenediamine salt and the like; inorganic acid salts such as citrate, tartrate, maleate, fumarate, mandelate, acetate, dichloroacetate, trifluoroacetate, dicloroacetate, trifluoroacetate, oxalate, formate and the like, sulfonates such as methanesulfonate, benzenesulfonate, p-toluenesulfonate and the like; and amino acid salts such as arginate, glutamate and the like. Acid addition salts include, but are not limited to, hydrochloric acid, fumaric acid, maleic acid, succinic acid, acetic acid, citric acid tartaric acid, phosphoric acid, oxalic acid, dichloroacetic acid and the like.

EXAMPLES

Figure 1:
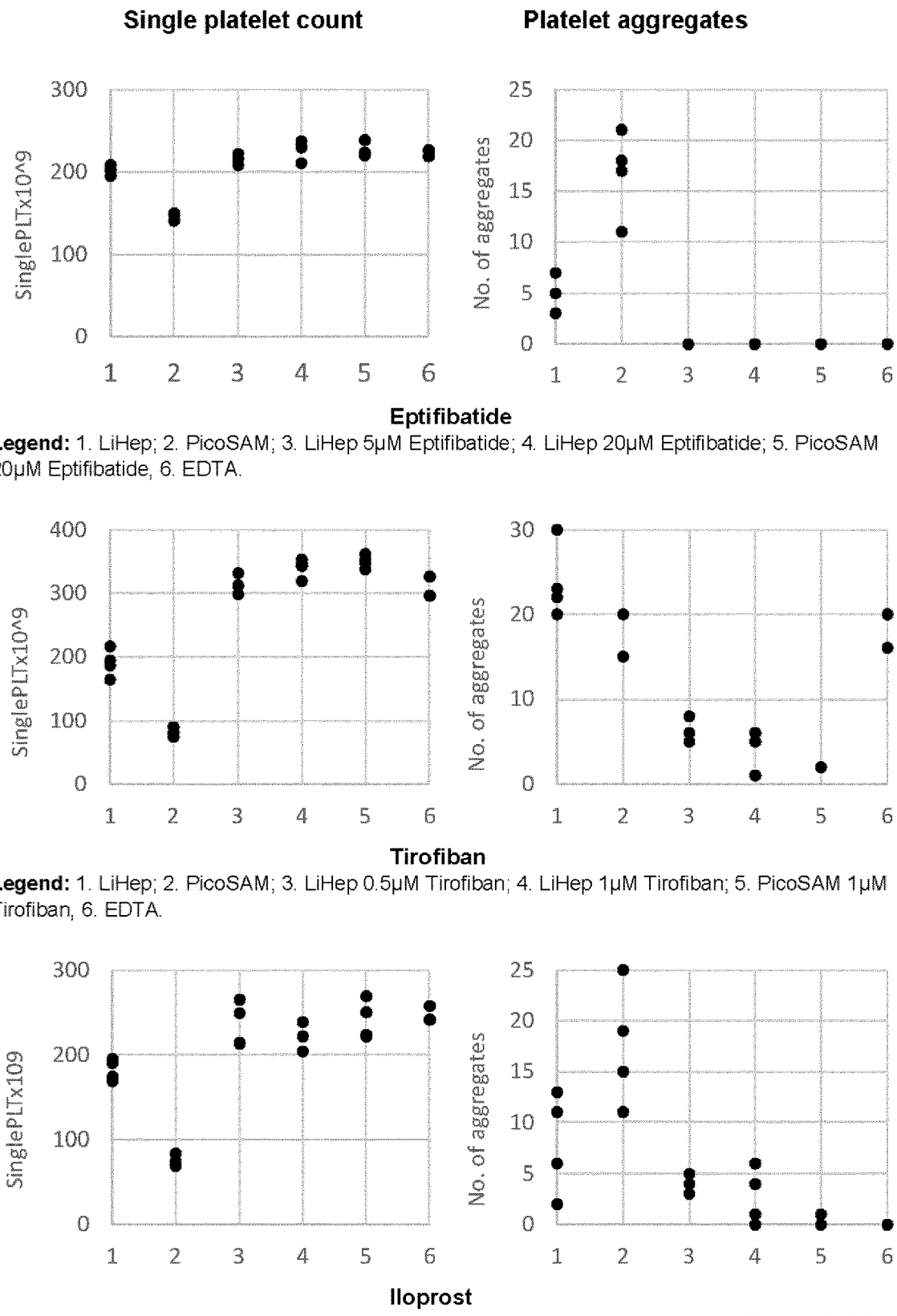
FIG. 1: Single platelet counts and number of platelet aggregates quantified in blood collected with PICO70 sampler containing only liquid heparin (LiHep, no gold-coated (Au) ball, gentle manual mixing), PICO70 mixed on SAM mixer (PicoSAM), EDTA anti-coagulant and liquid heparin or full PicoSAM in combination with two concentration levels of anti-platelet drugs eptifibatide, tirofiban or iloprost. The three anti-platelet drugs show single platelet counts and no or few aggregates comparable to standard EDTA anti-coagulated blood.

Example 1 Analysis of Platelet Aggregation Using Heparin and Different Anti-Platelet Agents Each experiment was conducted on a separate day with blood from one voluntary donor testing one anti-platelet drug candidate. For each experiment PICO70 syringe samplers (Radiometer Medical ApS) were prepared just before sample drawing. For "LiHep" (Liquid Heparin) conditions, PICO70 samplers were emptied of the gold ball and heparin brick and 15 µl of aqueous liquid balanced heparin comprising heparin lithium (Celsus Laboratories) and heparin sodium (Celsus Laboratories) (final heparin conc. 60 IU/mL blood) and 15 µl of the solvent of the tested drug were added. For "PicoSAM" conditions, unmodified PICO70 samplers (with gold ball and heparin brick) were used and 15 µl of the solvent of the respective tested drug was added. For "LiHep xxx drug" conditions, PICO70 samplers were emptied as described for LiHep and 15 µl of liquid balanced heparin (final heparin conc. 60 IU/mL blood) and 15 µl of the dissolved tested drug were added. For "PicoSAM xxx drug" conditions, unmodified PICO70 samplers (with gold ball and heparin brick) were used and 15 µl of the dissolved tested drug was added. The tested anti-platelet drug candidates and the corresponding solvents were eptifibatide acetate (Sigma, SML1042; dissolved in saline, final conc. 5 and 20 µM), $MgSO_4$ (Sigma, M7506; dissolved in saline, final conc. 3 and 12 mM), tirofiban hydrochloride monohydrate (Sigma, SML0246; dissolved in 1:200 DMSO in saline, final conc. 0.5 and 1 µM), iloprost (Sigma, SML1651; dissolved in 1:1000 or 1:10000 ethanol in saline, final conc. 10 and 100 nM (later also 1 µM)), ticlopidine hydrochloride (dissolved in saline, final conc. 60 and 600 µM), L-Arginine (Sigma, A5006; dissolved in saline, final conc. 600 µM and 6 mM) and dipyridamole (Sigma, D9766; dissolved in 1:10 or 1:100 DMSO in saline, final conc. 10 and 100 µM). An EDTA tube (BD Vacutainer with spray-coated $K_2$EDTA, 10 ml) and duplicate samples of all conditions of PICO70 syringe samplers were filled by drawing venous blood via a butterfly needle using a sealed VTC (vented tip cap) to fill the otherwise self-aspirating PICO70 samplers with 1.5 mL venous whole blood. Samplers were inverted 8 times immediately after drawing to insure proper anti-coagulation of the samples. The blood samples were mixed gently by hand (samplers without gold ball) or on a SAM mixer (Radiometer Medical ApS) for 15 minutes after drawing the sample. Mixed samples were fixed immediately with 10% formalin solution (1:1 dilution of blood in formalin) for at least 10 minutes and further diluted 1:10 in platelet dilution solution to hemolyze red blood cells (RBCs) to assessed manual platelet count using a hemocytometer. Manual platelet counts of single platelets (not aggregated), number of platelet aggregates and if possible, size (number of platelets in an aggregate) of platelet aggregates were quantified in duplicate on each sample by counting platelets in a hemocytometer using a Leica 750 microscope with 10× and 20× phase-contrast air objectives. Single platelet counts were adjusted for dilution with liquid heparin and or dissolved drug solution to calculate single platelet concentrations.

Eptifibatide, tirofiban and iloprost reduced the formation of platelet aggregates compared to "LiHep" and "PicoSAM" references (see FIG. 1).

Figure 2:
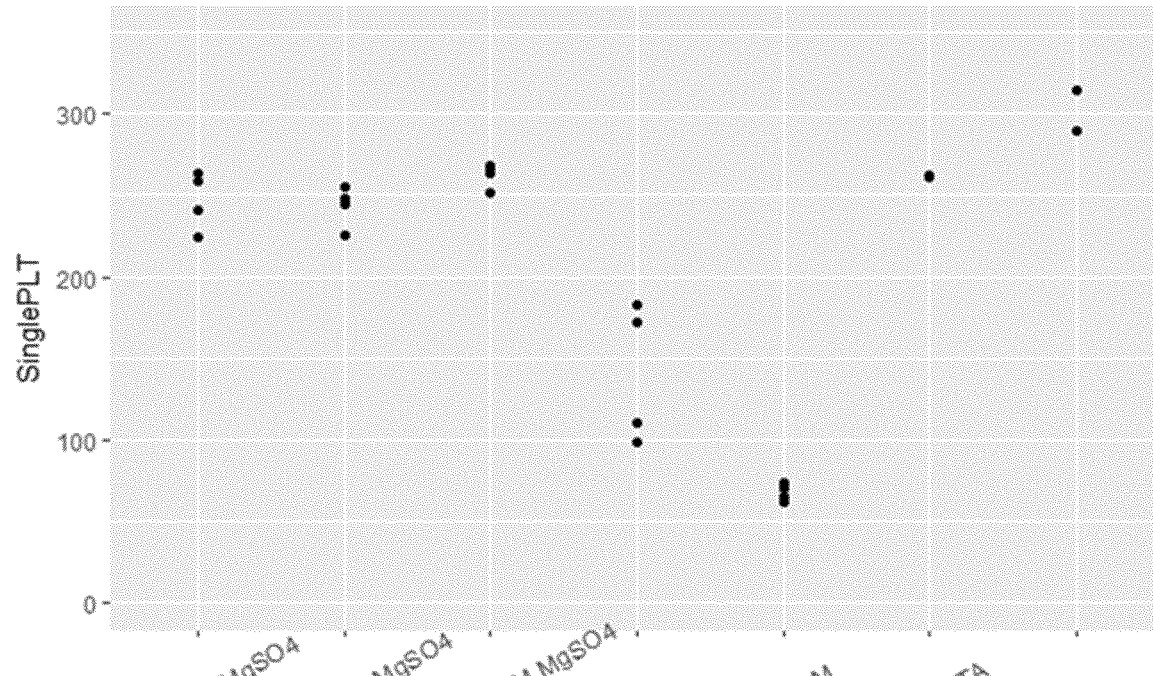
FIG. 2: Single platelet counts and number of platelet aggregates quantified in blood collected with PICO70 sampler containing only liquid heparin (LiHep, no Au ball, gentle manual mixing), PICO70 mixed on SAM mixer (PicoSAM), EDTA anti-coagulant and liquid heparin or full PicoSAM in combination with two concentration levels of anti-platelet drug $MgSO_4$.
Figure 2:
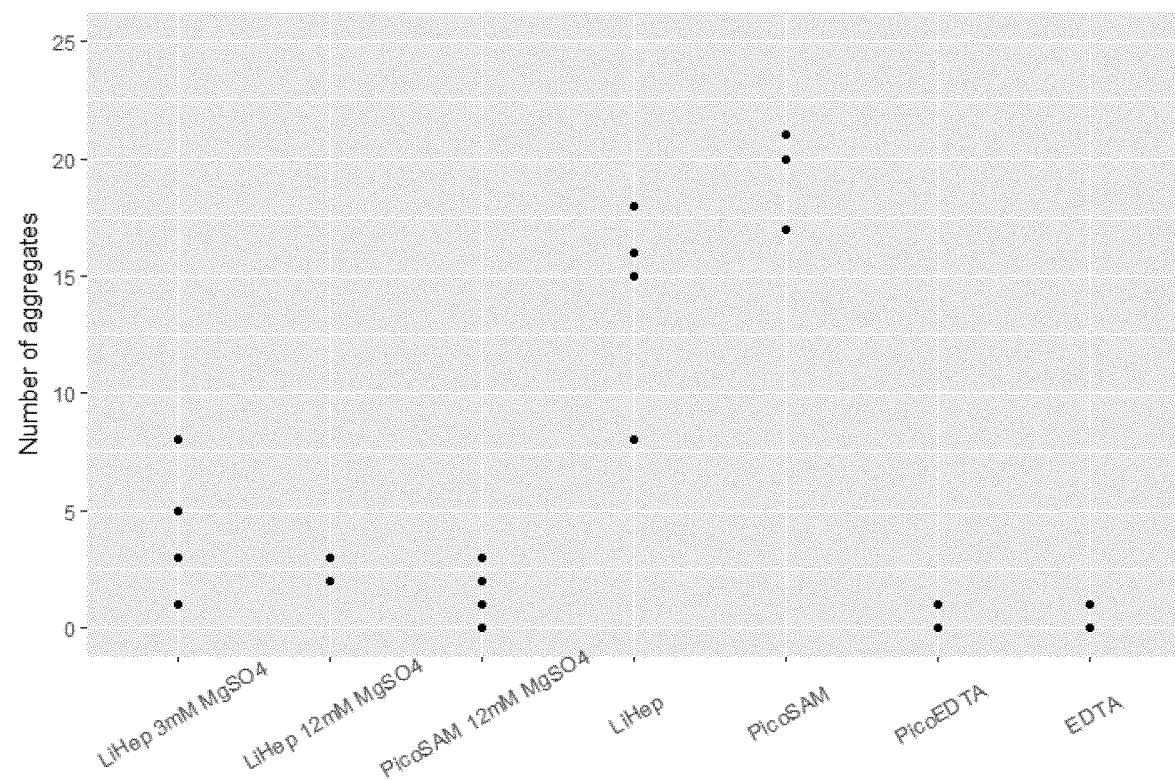

$MgSO_4$ also reduced the formation of platelet aggregates (see FIG. 2).

Figure 3:
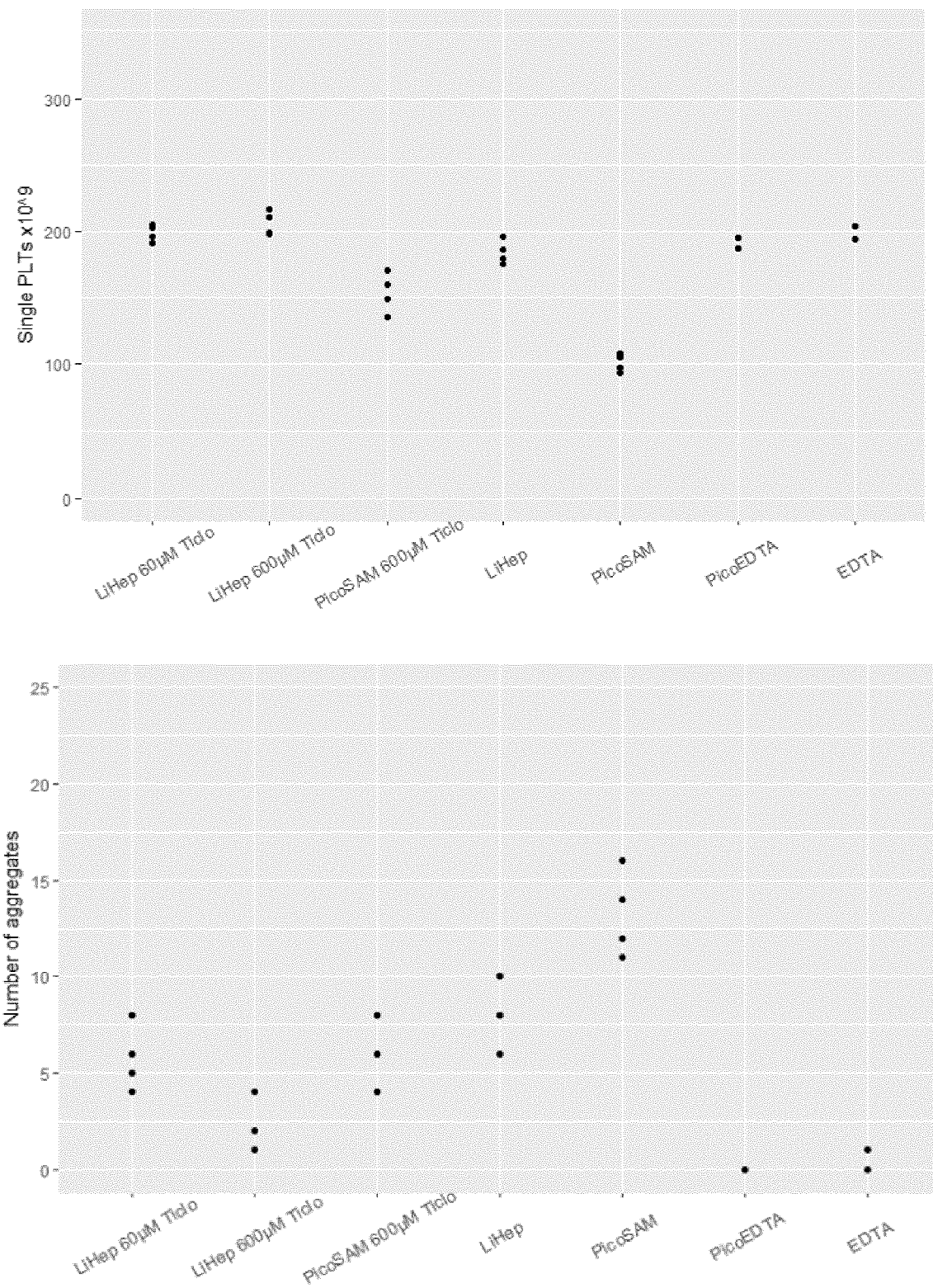
FIG. 3: Single platelet counts and number of platelet aggregates quantified in blood collected with PICO70 sampler containing only liquid heparin (LiHep, no Au ball, gentle manual mixing), PICO70 mixed on SAM mixer (PicoSAM), EDTA anti-coagulant and liquid heparin or full PicoSAM in combination with two concentration levels of anti-platelet drug ticlopidine.
Figure 4:
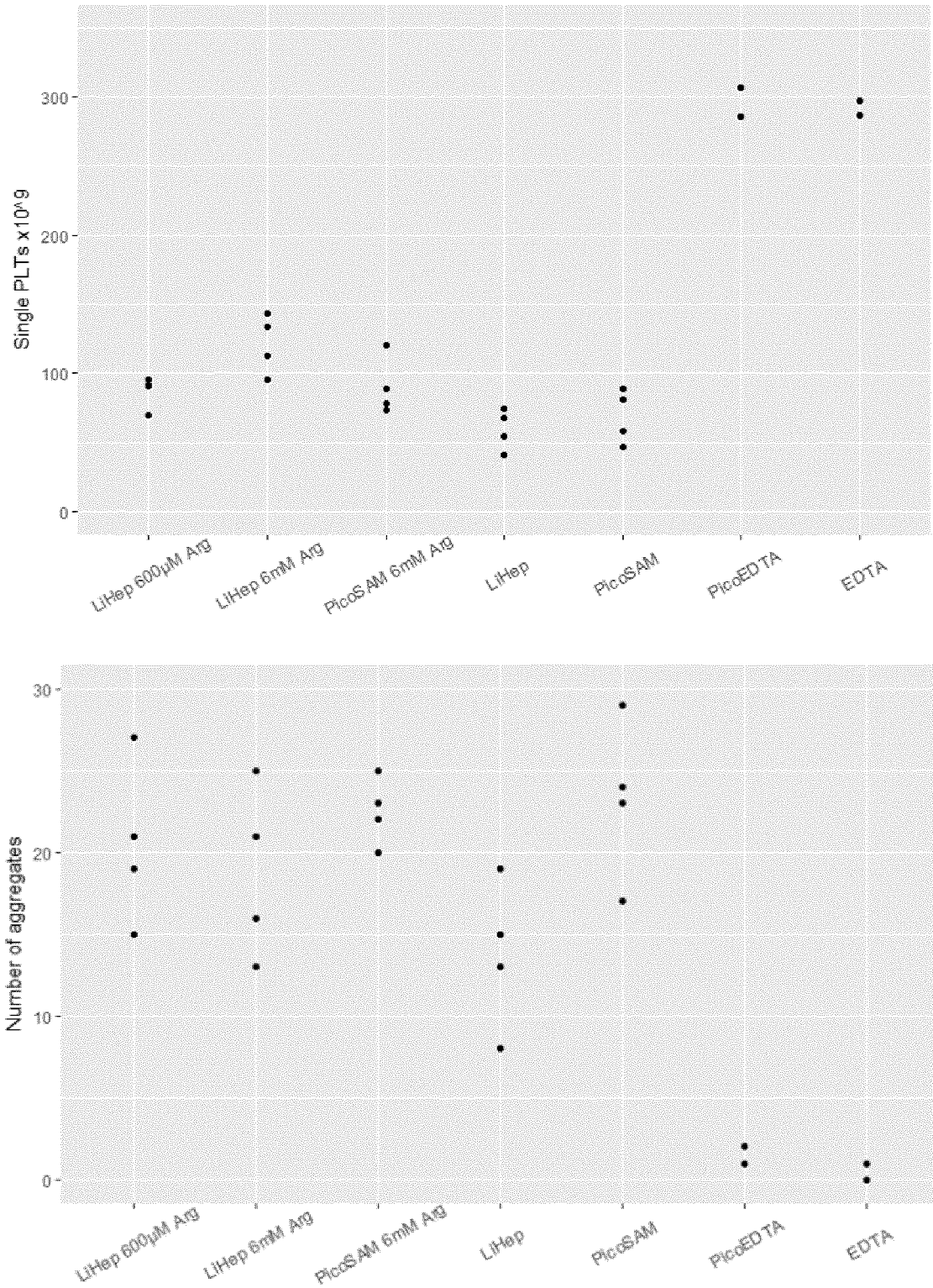
FIG. 4: Single platelet counts and number of platelet aggregates quantified in blood collected with PICO70 sampler containing only liquid heparin (LiHep, no Au ball, gentle manual mixing), PICO70 mixed on SAM mixer (PicoSAM), EDTA anti-coagulant and liquid heparin or full PicoSAM in combination with two concentration levels of anti-platelet drug L-Arginine.

Ticlopidine LiHep showed a similar count of single platelets compared to EDTA reference and a slightly reduced number of aggregates compared to the LiHep and PicoSAM controls (see FIG. 3). L-Arginine showed a decreased number of platelets and a higher number of platelet aggregates compared to EDTA control but still a slightly higher platelet count than the LiHep and PicoSAM controls (see FIG. 4).

Figure 5:
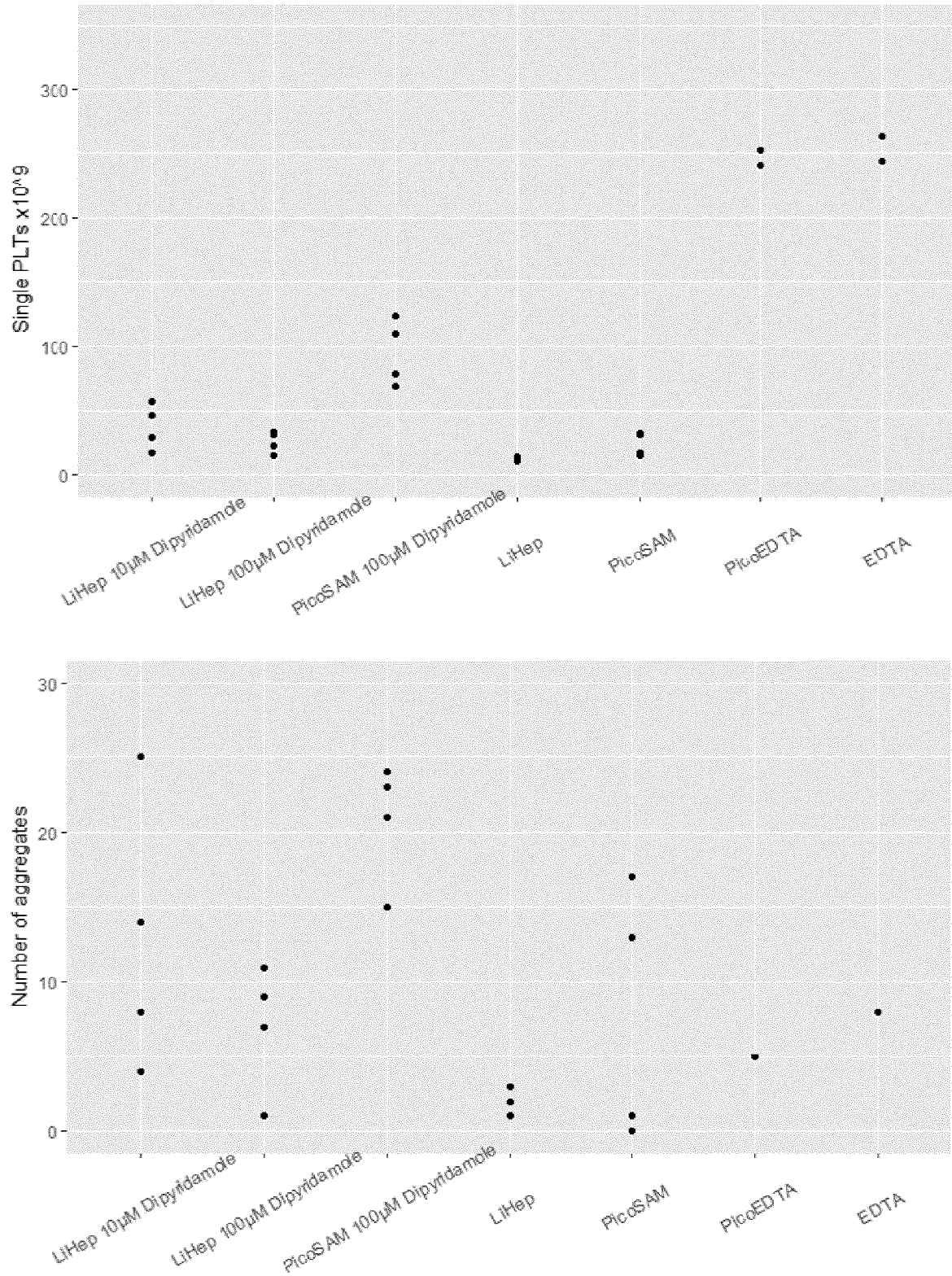
FIG. 5: Single platelet counts and number of platelet aggregates quantified in blood collected with PICO70 sampler containing only liquid heparin (LiHep, no Au ball, gentle manual mixing), PICO70 mixed on SAM mixer (PicoSAM), EDTA anti-coagulant and liquid heparin or full PicoSAM in combination with two concentration levels of anti-platelet drug dipyridamole.

Dipyridamole, a phosphodiesterase inhibitor and thromboxane inhibitor, showed a slightly higher platelet number compared to the LiHep and PicoSAM controls (see FIG. 5).

Example 2 Platelet Aggregation Studies with Heparinized Blood and EDTA-Treated Blood Venous blood samples drawn, mixed and fixed with 10% formalin solution, as described before in Example 1 were used to prepare wet mounts on a glass slide and covered with a glass coverslip. Wet mount samples of fixed blood cells were then imaged with a Leica 750 microscope using a 40× phase-contrast air objective. Aggregated platelets in heparinized blood versus non-aggregated single platelets in EDTA anti-coagulated blood and heparinized blood with e.g. eptifibatide are seen between abundant RBCs.

Figure 6:
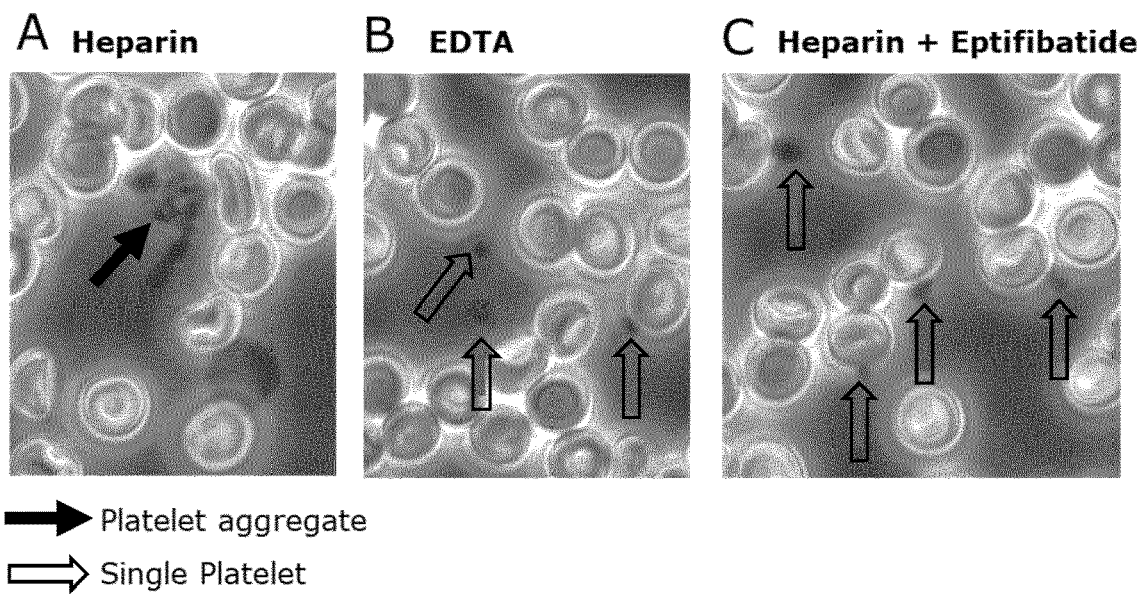
FIG. 6: Microscopic images of blood samples anti-coagulated with (A) heparin and (B) EDTA. While EDTA prevents platelet activation and maintains single platelets in the blood sample, heparin allows or even potentiates platelet aggregation induced by other agonists or foreign materials. This effect of heparin cannot be observed in microscopic images when (C) 20 µM eptifibatide is added to the heparin.

The results are shown in FIG. 6. Heparinized blood showed platelet aggregates which cannot be seen in blood samples prepared with EDTA or in a blood sample prepared with heparin and an antiplatelet drug such as eptifibatide.

Example 3 Wet Mount Images of Stained Blood Samples

Venous blood samples were drawn and mixed as described before in Example 1 and used to prepare stained wet mounts images. Blood samples were mixed with a staining and hemolyzing agent (methylene blue and deoxycholic acid, respectively) and incubated at 47° C. in a water bath for 30 seconds. Stained and hemolyzed blood samples were then prepared in wet mount samples on a glass slide and covered with a glass coverslip. Images of stained samples were then acquired with a Leica 750 microscope using a 40× air objective in bright field mode. An image processing software (FIJI, ImageJ) was used to select regions of interest (ROIs) of representative stained WBCs from the images.

PicoSAM samples (heparinized blood without an antiplatelet drug) showed many aggregated platelets (small roundish cells).

Figure 7:
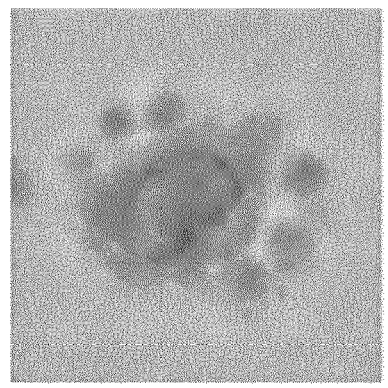
FIG. 7: Blood sample handmixed with staining/hemolyzing reagent. Stained WBCs (white blood cells) and platelets prepared in a wet mount on a glass coverslip were imaged with a Leica microscope using a 40× objective in bright field mode. (A) Example of white blood cells showing interaction with platelets. (B) Example of white blood cell aggregates.
Figure 7:
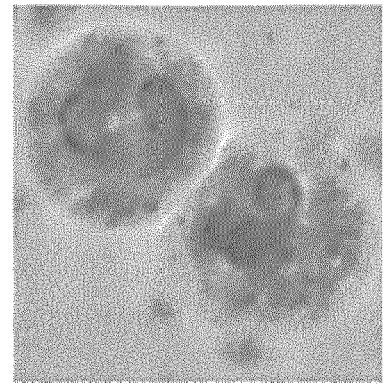

PicoSAM samples with 1 µM tirofiban or 20 µM eptifibatide showed single platelets but also platelet satellinism, i.e. platelets binding to WBCs. This is for example shown in FIG. 7A. Further, WBC aggregates were also observed as shown in FIG. 7B.

PicoSAM samples with 100 nM iloprost (or samples with balanced LiHep and 100 nM Iloprost) showed single platelets, not platelet satellinism or WBC aggregates. The same results were obtained using EDTA anti-coagulated blood.

Example 4 Single Platelet Concentrations of Iloprost Heparin Samples Compared to EDTA Reference Samples Manual Platelet Count
    Samples were prepared as described in Example 1.
ABX Platelet Count
    Blood samples drawn and mixed after 15 minutes as described above were assessed with an automated hematology analyzer (Horiba, ABX Pentra 60C+) (ABX) for complete blood count (CBC) with 5-diff including WBC concentration, platelet concentration, mean platelet volume (MPV), concentrations and fractions of neutrophils, lymphocytes, monocytes, eosinophils and basophils, RBC concentration, hematocrit, hemoglobin concentration, RBC descriptive parameters (MCV, MCH, MCHC, RDW). Samples were prepared from several donors. Measured platelet concentration was used to compare to manually assessed platelet concentrations of iloprost heparin samples (in PICO70 samplers) and EDTA anti-coagulated samples. For control, EDTA samples with no platelet aggregates are used as reference measurement for the measured automated ABX platelet concentration.

For one donor, the average performance of platelet count of PicoSAM 100 nM iloprost samples compared to EDTA samples as reference was 97% for the manual count.

For eight donors, the average performance of platelet count of PicoSAM 1 µM iloprost samples compared to EDTA samples as reference was 93% for the manual count.

The respective PicoSAM sample, i.e. without iloprost but with heparin, in contrast showed a performance of less than 40% compared to the EDTA reference.

For seven donors, the average performance of platelet count of PicoSAM 1 µM iloprost samples compared to EDTA samples as reference was 97% for the ABX platelet count.

Table 1 shows the results of platelet counts for donors samples where both types of platelet counts (manual and ABX platelet count) were performed.

TABLE 1

Comparison platelet count

| Donor ID | | Mean ABX PLT count (PLT/nl) | Mean Manual PLT count (PLT/nl) |
|---|---|---|---|
| 4 | PicoSAM Iloprost 1 µM | 204 | 198 |
|   | EDTA | 200 | 200 |
| 5 | PicoSAM Iloprost 1 µM | 253 | 242 |
|   | EDTA | 259 | 242 |
| 6 | PicoSAM Iloprost 1 µM | 173 | 154 |
|   | EDTA | 185 | 189 |
| 7 | PicoSAM Iloprost 1 µM | 233 | 247 |
|   | EDTA | 240 | 249 |
| 8 | PicoSAM Iloprost 1 µM | 191 | 203 |
|   | EDTA | 202 | 207 |
| 9 | PicoSAM Iloprost 1 µM | 216 | 202 |
|   | EDTA | 236 | 255 |

Example 5 Anti-Platelet Drug Interference Test on ABL90 Parameters

Each experiment was conducted on a separate day with blood from one voluntary donor. For each experiment three PICO70 syringe samplers (Radiometer Medical ApS) (not modified, containing a gold ball and a heparin brick) were prepared. One PICO70 was used unmodified (Ctrl), one PICO70 was filled with 15 µl of dissolved anti-platelet drug to reach the indicated final concentration in the blood sample. A third PICO70 sampler was filled with 15 µl of solvent (specific solvent, which is used to dissolve the tested anti-platelet drug: reference sample). Venous blood samples were drawn into PICO70 syringe samplers via a butterfly needle and a sealed vented tip cap (VTC) to fill the self-aspirating PICO70 samplers with 1.5 ml whole blood. Samplers were inverted eight times immediately after drawing to insure proper heparinization of the sample. The blood samples were mixed on a SAM mixer (Radiometer Medical ApS), moving the gold-coated steel ball through the blood sample in order to ensure homogenous and reproducible mixing for 15 minutes after drawing of the blood, and analyzed on an ABL90 blood gas analyzer (Radiometer Medical ApS). Samples were measured in alternating order (Ctrl, Reference sample, Drug sample) five times each (5 replicate measurements) with gentle manual inversion of the samples in order to keep blood samples homogenously mixed through the measurements. All calculated values are described in Table 3. Afterwards blood samples were centrifuged to separate the plasma fraction. Plasma of all samples was measured in triplicate in alternating order on the ABL90 instrument to assess the free Hemoglobin concentration in the plasma, which indicates a possible problematic hemolyzation of red blood cells (RBCs) in the whole blood sample. Hemolyzed samples show interference on e.g. the measured $K^+$ concentration.

Measured parameters are described in Table 2.

TABLE 2

Parameters measured with ABL90 blood gas analyzer

| Parameter | Description |
|---|---|
| pH | pH |
| tHb (g/dL) | total Hemoglobin concentration |
| COHb (%) | Carboxyhemoglobin (carboxylated Hemoglobin) |
| MetHb (%) | Methemoglobin (methylated Hemoglobin) |
| $K^+$ (mmol/L) | Potassium concentration |
| $Na^+$ (mmol/L) | Sodium concentration |
| $Ca^{2+}$ (mmol/L) | Calcium concentration, ionized |
| $Cl^-$ (mmol/L) | Chloride concentration |
| Glu (mmol/L) | Glucose concentration |
| Lac (mmol/L) | Lactate concentration |
| tBil (µmol/L) | Bilirubin concentration |

The nomenclature of how the calculations have been made is described in Table 3 and the nomenclature of the measured samples is described in Table 4.

TABLE 3

Calculated values

| | |
|---|---|
| Mean | Mean value of 5 replicate measurements performed on the same whole blood sample or 3 replicate measurements of Hemoglobin measured on plasma sample (data not shown) |
| SD | Standard deviation calculated from 5 replicate measurements (data not shown) |
| Difference | Difference in measured parameter between indicated samples (test sample with drug − reference sample with solvent only) (data not shown) |
| Fraction of maximum interference | Difference divided by maximum allowed interference for each parameter (a value >1 indicates an interference, whereas <1 are acceptable) |

TABLE 4

Sample names

| | |
|---|---|
| Ctrl | Control sample drawn into unmodified PICO70 syringe sampler |
| Saline | Reference sample containing solvent saline (physiological NaCl solution) |
| DMSO/Saline (1:200) | Reference sample containing solvent DMSO in saline (1:200 dissolved) |
| EtOH/Saline (1:1000) | Reference sample containing solvent ethanol (EtOH) in saline (1:1000 dissolved) |
| EtOH/Saline (1:100) | Reference sample containing solvent ethanol (EtOH) in saline (1:100 dissolved) |
| Eptifibatide 20 uM in saline | Eptifibatide dissolved in saline to reach final conc. of 20 µM eptifibatide in the blood sample |
| Tirofiban 1 uM in DMSO/Saline | Tirofiban dissolved inDMSO/saline solvent (1:200) to reach final conc. of 1 µM tirofiban in the blood sample |
| Iloprost 100 nM in EtOH/Saline | Iloprost dissolved in ethanol/saline solvent (1:1000) to reach final conc. of 100 nM iloprost in the blood sample |
| Iloprost 1 uM in EtOH/Saline | Iloprost dissolved in ethanol/saline solvent (1:100) to reach final conc. of 1 µM iloprost in the blood sample |
| $MgSO_4$ 12 mM in saline | $MgSO_4$ dissolved in saline to reach final conc. of 12 mM $MgSO_4$ in the blood sample |

Reference range for adults and maximum interference allowed in the examples are shown in Table 5.

The results of the measurements (as fraction of maximum interference) are summarized in Table 6.

TABLE 5

Reference values for determining maximum allowed interference.

| | pH | tHb (g/dL) | COHb (%) | MetHb (%) | $K^+$ (mmol/L) | $Na^+$ (mmol/L) |
|---|---|---|---|---|---|---|
| Reference range adult | 7.32-7.43 | 11.4-17.5 | 2-3% (non-smokers) 7-9% (smokers) | 1-2% | 3.4-4.5 | 136-145 |
| max. Interference allowed | <0.010 | <0.5 | <1% | <1% | <0.1 | <1 |

| | $Ca^{2+}$ (mmol/L) | Cl— (mmol/L) | Glu (mmol/L) | Lac (mmol/L) | tBil (µmol/L) |
|---|---|---|---|---|---|
| Reference range adult | 1.15-1.33 | 98-107 | 3.6-5.3 | 0.56-1.39 | 0-34 |
| max. Interference allowed | 0.02 | 1 | 0.1 | 0.1 | 30 |

TABLE 6

Fraction of maximum interference of parameter for antiplatelet drugs

| | Eptifibatide | Tirofiban | Iloprost | $MgSO_4$ |
|---|---|---|---|---|
| pH | 0.18 | 0.18 | 0.32 | 5.56 |
| tHb (g/dL) | 0.04 | 0.12 | 0.12 | 0.08 |
| COHb (%) | 0.02 | 0.06 | 0.08 | 0.04 |
| MetHb (%) | 0.08 | 0.04 | 0.04 | 0.04 |
| $K^+$ (mmol/L) | 0 | 0 | 0.18 | 2.0 |
| $Na^+$ (mmol/L) | 0.4 | 0 | 0.14 | 5.6 |
| $Ca^{2+}$ (mmol/L) | 0.2 | 0.1 | 0.1 | 2.7 |
| $Cl^-$ (mmol/L) | 0 | 0 | 0.06 | 8.6 |
| Glu (mmol/L) | 0 | 0.8 | 0.86 | 0.2 |
| Lac (mmol/L) | 0.6 | 0 | 0.62 | 4.6 |
| tBil (µmol/L) | 0.013 | 0.000 | 0.013 | 0.140 |

Eptifibatide, tirofiban and iloprost showed no interference on assessed ABL parameters, whereas $MgSO_4$ shows interference (Difference Fraction max. Interf. >2) on multiple parameters (pH, $N^+$, $K^+$, $Ca^{2+}$, $Cl^-$, and Lac).

Eptifibatide, tirofiban and iloprost should therefore be safe to add to heparinized blood used for measurement of blood gas and basic metabolic panel parameters at the tested concentrations.

Example 6 Robustness of Samples Against Pre-Analytical Stress

A test of sample robustness against stress conditions was performed, comparing blood samples with heparin (lithium heparin 18 IU/ml) only and blood samples with heparin (lithium heparin 18 IU/ml)+ iloprost (1 microM).

Shortly after blooddraw, the blood from the vacutainer tubes was aspirated into marked SafePicoAsp syringes (1.5 ml), placed in a plastic bag and fully emerged into icecubes for 30 minutes. After 30 minutes, the syringes were removed and shaken for 30 seconds by fast lengthwise movements back and forth, approx. 4/sec. Every syringe was mixed gently (by slow inversions by twisting the wrist, approx. 1/sec) prior to aspiration on analyzers. The resulting samples were aspirated on nine ABL90 analyzers approximately 400 times each and instances of clots were recorded. All samples were aspirated from picosafe samplers. The results are shown in Table 7.

TABLE 7

Clots detected in samples exposed to low temperature and shaking.

| | Total number of aspirations | Clots (Error # 1271) | Frequency |
|---|---|---|---|
| Heparin | 452 | 5 | 1.11% |
| Heparin + Iloprost | 416 | 1 | 0.24% |

The clot frequency was 4-5 times higher in the samples without Iloprost.

A further experiment was conducted with larger blood volumes using 9 ml Greiner Bio-one Vaceutte vacuum tubes. Shortly after blooddraw, the vacutainer tubes were placed on ice for 30 minutes. Subsequently, the vacutainer tubes were tempered to ambient temperature and mixed gently before centrifugation for 3 minutes at 1500 G to imitate sedimentation. After centrifugation, the blood was pooled and distributed into 2×3 marked 20 ml syringes and tested on 10 ABL90 analyzers via robot. The samples were aspirated using large 20 ml samples (robots). The results are shown in Table 8.

TABLE 8

Clots detected in samples exposed to low temperature and shaking.

| | Total number of aspirations | Clots (Error # 1271) | Frequency |
|---|---|---|---|
| Heparin | 707 | 7 | 0.99% |
| Heparin + Iloprost | 659 | 0 | 0% |

Again, the clot frequency was higher in the sample without Iloprost.

The invention claimed is:

1. An in vitro method for determining a basic metabolic panel (BMP) parameter in a blood sample comprising:
    i) combining the blood sample with an anti-coagulant and an antiplatelet agent, and
    ii) determining said BMP parameter in the blood sample, wherein the blood sample, prior to the determination in ii), has been subjected to pre-analytical stress,
    wherein the anti-coagulant is heparin and the antiplatelet agent is Iloprost, and
    wherein the method does not comprise combining $MgSO_4$, EDTA, or citrate with blood of the blood sample.

2. The in vitro method according to claim 1, wherein ii) is performed in a sensor assembly comprising two or more analyte sensors.

3. The in vitro method according to claim 2, wherein said two or more analyte sensors are not all positioned in the same plane, and wherein a first one of said two or more analyte sensors analyzes said BMP parameter, and wherein a second one of said two or more analyte sensors that is not located in the same plane as the first one analyzes a different BMP parameter.

4. The in vitro method according to claim 1, wherein said pre-analytical stress comprises exposure to a temperature between −5° C. and 20° C.

5. The in vitro method according to claim 1, wherein a volume used for the determination in ii) is less than 1 ml.

6. The in vitro method according to claim 1, wherein i) further comprises mixing the blood sample.

7. The in vitro method according to claim 1, wherein the method is for determining a BMP parameter and wherein the BMP parameter is selected from the group consisting of $Na^+$, $K^+$, $Mg^{2+}$, $Cl^-$, $HCO_3^-$, urea, creatinine, glucose, $Ca^{2+}$, lactate, and total bilirubin.

8. The in vitro method according to claim 1, wherein the method further comprises determining platelet count and/or white blood cell count in the blood sample obtained in i).

9. The in vitro method according to claim 1, wherein the preanalytical stress comprises exposure to a temperature below 20° C., by contact with air, and/or by shear forces.

10. The in vitro method according to claim 4, wherein said preanalytical stress comprises exposure to a temperature between −5° C. and 15° C.

11. The in vitro method according to claim 4, wherein said preanalytical stress comprises exposure to a temperature between 0° C. and 5° C.

12. The in vitro method according to claim 1, wherein a volume used for the determination in ii) is less than 200 microliters.

13. The in vitro method according to claim 1, wherein the method is for determining two or more BMP parameters, and ii) comprises simultaneously determining said two or more BMP parameters.

14. An in vitro method for determining a BMP parameter in a blood sample comprising:

i) combining the blood sample with an anti-coagulant and an anti-platelet agent, ii) exposing the blood sample to a temperature below 20° C., and iii) determining said BMP parameter in the blood sample, wherein the anti-coagulant is heparin and the antiplatelet agent is Iloprost, and wherein the method does not comprise combining $MgSO_4$, EDTA, or citrate with blood of the blood sample.

15. The in vitro method according to claim 14, wherein a volume used for the determination in iii) is less than 1 ml.

16. The in vitro method according to claim 14, wherein iii) is performed in a sensor assembly comprising two or more analyte sensors.

17. The in vitro method according to claim 16, wherein said two or more analyte sensors are not all positioned in the same plane, and wherein a first one of said two or more analyte sensors analyzes said BMP parameter, and wherein a second one of said two or more analyte sensors that is not located in the same plane as the first one analyzes a different BMP parameter.

18. The in vitro method according to claim 14, wherein the method further comprises determining platelet count and/or white blood cell count in the blood sample obtained in i).

19. The in vitro method according to claim 14, wherein the method is for determining a BMP parameter and wherein the BMP parameter is selected from the group consisting of $Na^+$, $K^+$, $Mg^{2+}$, $Cl^-$, $HCO_3^-$, urea, creatinine, glucose, $Ca^{2+}$, lactate, and total bilirubin.

20. The in vitro method according to claim 14, wherein the method is for determining two or more BMP parameters, and iii) comprises simultaneously determining said two or more BMP parameters.

* * * * *